(12) United States Patent
Bergmann et al.

(10) Patent No.: US 7,723,489 B1
(45) Date of Patent: May 25, 2010

(54) USE OF BLOCKING ANTI-TSH-RECEPTOR-ANTIBODIES IN THE THERAPY OF HYPERTHYREOSES AND MONOCLONAL ANTIBODIES FOR A USE OF THIS TYPE

(75) Inventors: Andreas Bergmann, Berlin (DE); Joachim Struck, Berlin (DE); Nils Gernot Morgenthaler, Berlin (DE); Alan P. Johnstone, Surrey (GB); Philip S. Shepherd, Surrey (GB)

(73) Assignee: B.R.A.H.M.S. Aktiengesellschaft, Hennigsdorf (DE)

( * ) Notice: Subject to any disclaimer, the term of this patent is extended or adjusted under 35 U.S.C. 154(b) by 0 days.

(21) Appl. No.: 09/889,094

(22) PCT Filed: Feb. 18, 2000

(86) PCT No.: PCT/EP00/01304
§ 371 (c)(1),
(2), (4) Date: Oct. 19, 2001

(87) PCT Pub. No.: WO00/49050
PCT Pub. Date: Aug. 24, 2000

(30) Foreign Application Priority Data
Feb. 19, 1999 (DE) ................................. 199 07 094

(51) Int. Cl.
*C07K 16/12* (2006.01)
(52) U.S. Cl. ............................... 530/388.22; 530/388.1
(58) Field of Classification Search ........................ None
See application file for complete search history.

(56) References Cited

U.S. PATENT DOCUMENTS

| | | | |
|---|---|---|---|
| 5,614,192 A * | 3/1997 | Vandenbark | 424/185.1 |
| 5,639,670 A | 6/1997 | Bergmann et al. | |
| 5,814,461 A | 9/1998 | Bergmann et al. | |
| 6,228,597 B1 | 5/2001 | Parmentier et al. | |
| 6,747,139 B1 * | 6/2004 | Rapoport et al. | 536/23.5 |
| 7,015,003 B1 | 3/2006 | Bergmann et al. | |

2006/0165676 A1  7/2006  Bergmann et al.

OTHER PUBLICATIONS

Nicholson, L.B. et al: "Monoclonal antibodies to the human TSH receptor: epitope mapping and binding to the native receptor on the basolateral plasma membrane of thyroid follicular cells" J. Mol. Endocrinol. (1996), 16(2), 159-170 XP000943987 the whole document.
Seetharamaiah, Gattadahalli S. et al: "Generation and characterization of monoclonal antibodies to the hyman thyrotropin (TSH) receptor: antibodies can bind to discrete conformationa or linear epitopes and block TSH binding" Endocrinology (1995). 136(7). 2817-24. XP000944028 the whole document.
Shepherd, P.S. et al: "Identification of an important thyrotrophin binding site on the human thyrotrophin receptor using monoclonal antibodies" Mol. Cell. Endocrinol. (Mar. 25, 1999), 149(1-2), 197-206, XP000944024 the whole document.
Nicholson et al., "Monoclonal antibodies to the human TSH receptor: epitope mapping and binding to the native receptor on the basolateral plasma membrane of thyroid follicular cells", Journal of Molecular Endrocrinology (1996), vol. 16, 159-170.
Seetharamaiah et al., "Generation and Characterization of Monoclonal Antibodies to the Human Thyrotropin (TSH) Receptor: Antibodies Can Bind to Discrete Conformational or Linear Epitopes and Block TSH Binding", Endocrinology, 1995, vol. 136(7), 2817-2824.
Shepherd et al., "Identification of an important thyrotrophin binding site on the human thyrotrophin receptor using monoclonal antibodies", Molecular and Cellular Endocrinology vol. 149 (1999), 197-206.
Orgiazzi et al., "Thyroid-stimulating hormone receptor and thyroid diseases", Revue Du Praticien, 1994, vol. 44(9), 1184-91. (English Abstract on p. 1191).

* cited by examiner

*Primary Examiner*—Michael Pak
(74) *Attorney, Agent, or Firm*—Heslin Rothenberg Farley & Mestiti P.C.

(57) ABSTRACT

Use of blocking antibodies against the human TSH receptor (hTSH receptor) or their specifically binding fragments for the treatment of, or for preparation of drugs for the treatment of, hyperthyroidism which is attributable to stimulating autoantibodies against the hTSH receptor (Graves' disease) or overstimulation of the thyroid gland by endogenous TSH or to activating mutations of the hTSH receptor, and for the treatment of Graves' ophthalmopathy, and specific blocking monoclonal antibodies which recognize the minimum sequence FDSH corresponding to the positions 381 to 384 of the human TSH receptor.

2 Claims, 3 Drawing Sheets

USE OF BLOCKING ANTI-TSH-RECEPTOR-ANTIBODIES IN THE THERAPY OF HYPERTHYREOSES AND MONOCLONAL ANTIBODIES FOR A USE OF THIS TYPE

The present invention relates to the use of blocking anti-TSH receptor antibodies in the therapy of hyperthyroidism, such as Graves' disease, i.e. for the treatment of, or for the preparation of drugs for the treatment of, such diseases, and monoclonal antibodies particularly suitable for such a use.

It is known that numerous diseases in which the thyroid is involved are autoimmune diseases in which autoantibodies against molecular structures of the thyroid are formed and, in association with the disease, begin to act as autoantigens. The most important known autoantigens of the thyroid are thyroglobulin (Tg), thyroid peroxidase (TPO) and in particular TSH receptors (TSHr) (cf. Furmaniak J. et al., Autoimmunity 1990, Vol. 7, pages 63-80).

The TSH receptor is a receptor which is localized in the thyroid membrane and to which the hormone TSH (thyroid-stimulating hormone or thyrotropin) which is secreted by the pituitary gland binds and thus triggers the secretion of the actual thyroid hormones, in particular of thyroxin. The TSH receptor belongs to the receptor family comprising the G-protein-coupled glycoprotein receptors having a large amino-terminal extracellular domain, to which the LH/CG receptor and the FSH receptor also belong. An elucidation of the chemical structure of the TSH receptor, i.e. of the sequence of the DNA coding for it and of the amino acid sequence of the receptor itself which is derivable therefrom, was achieved at the end of 1989 (cf. Libert F. et al., Biochem. Biophys. Res. Commun. 165: 1250-1255; Nagayama Y. et al., Biochem. Biophys. Res. Commun. 165: 1184-1190; cf. also EP-A-0433509 and WO-A-91/09121; and WO-A-91/09137; WO-A-91/10735 and WO-A-91/03483; furthermore Yuji Nagayama & Basil Rapoport in: Molecular Endocrinology, Vol. 6 No. 2, pages 145-156, and the literature cited therein).

Owing to the formation of autoantibodies against the TSH receptor (also generally abbreviated to TRAb) in the course of various thyroid autoimmune diseases, the determination of such autoantibodies is of considerable clinical importance, in particular for the diagnosis of Graves' disease.

Apart from methods of determination in which experimental animals or special cell cultures play a role and are primarily of historical interest today (cf. Schumm-Draeger et al., Akt. Endokr. Stoffw. 10 (1989), pages 90-102), it has been possible to date to determine TSH receptor autoantibodies essentially according to two basic methods (cf. Morgenthaler N. G. et al., Horm. Metab. Res. 30 (1998), pages 162-168):

In cell stimulation tests, the presence of stimulating TSH receptor autoantibodies, which are frequently referred to in the literature by the abbreviation TSHb or TSI (TSI=thyroid stimulating immunoglobulins), manifests itself by the fact that specific functions of suitable cells which have natural or recombinant TSH receptors in their cell membrane and come into contact with TSH and/or with an autoantibody-containing sample are triggered or enhanced by stimulation, in particular the formation of cAMP (cyclic adenosine monophosphate). Blocking TSH receptor antibodies (TBAb) can be detected from the decrease in the action of TSH. Since such bioassays are very complicated to carry out, their importance today lies not so much in the area of routine clinical diagnosis as in that of basic research. They are a valuable aid in the elucidation of the exact type of interaction between antibodies and the functional fine structure of the TSH receptor. Thus, the publication by N. G. Morgenthaler et al. in Horm. Metab. Res. 30 (1998), pages 162-168, describes how specific CHO cells which were transformed in such a way that they express the complete recombinant TSH receptor and which are referred to as JP09 CHO cells (Perret J et al., Biochem Biophys Res Commun 1990; 171: 1044-50) can be successfully used for detecting and distinguishing from one another stimulating (TSAb) and/or blocking autoantibodies (TBAb) in unfractionated sera or IgG fractions obtainable therefrom by purification and for determining the occurrence of said autoantibodies and their relative proportions in a biological sample. The methodology described in said publication is referred to below in the experimental section, and the entire content of this publication and the further publications stated therein as literature citations are hereby expressly incorporated by reference to supplement the present description and as further more detailed literature.

Alternatively, TSH receptor autoantibodies (TRAb) can also be determined using competitive receptor binding assays, in particular radioreceptor assays, for example using the TRAK Assay® of B.R.A.H.M.S Diagnostika GmbH. For the determination of TSH receptor autoantibodies by the conventional variant of this method, the autoantibodies to be determined and originating from a serum sample are allowed to compete in the liquid phase with a radiolabelled bovine TSH competitor for the binding sites of a detergent-solubilized porcine TSH receptor (cf. Southgate, K. et al., Clin. Endocrinol. (Oxford) 20, 539-541 (1984); Matsuba T. et al., J. Biochem. 118, pages 265-270 (1995); EP 719 858 A2; product information on TRAK-Assay® of B.R.A.H.M.S Diagnostika GmbH). In order to determine the labelled TSH bound to the receptor preparation, after the end of the incubation the TSH receptor is separated from the liquid phase by means of a precipitating reagent and a subsequent centrifuging step. The determination of the receptor-bound labelled TSH is carried out by measuring the radioactivity bound in the sediment. Since the determination is based on competition between labelled TSH and the antibodies to be determined for common binding sites on the TSH receptor, this method determines all those autoantibodies, and only those autoantibodies, which actually compete with TSH. Such competing autoantibodies capable of inhibiting the TSH binding are also referred to in the literature as TBII (TBII=thyrotropin-binding inhibitory immunoglobulin), and the extent of their activity is also stated as percentage so-called TBII activity.

It has long been known that heterogeneous autoantibody populations of different compositions are formed in autoimmune diseases of the thyroid gland. The stimulating autoantibodies and the autoantibodies competing with TSH are identical only in some cases, i.e. there are stimulating autoantibodies which do not compete with TSH and there are also autoantibodies competing with TSH which do not have a stimulating effect. The heterogeneity of the autoantibody populations led to the situation where, with the earlier radioreceptor assays for detecting autoantibodies against the TSH receptor, such autoantibodies were detectable only in 80-90% of patients suffering from Graves' disease. Only with the modern receptor binding assays of the so-called "second generation", in which preparations of suitable recombinant human TSH receptors and selected monoclonal antibodies for immobilizing them are used instead of porcine TSH receptor preparations, are autoantibodies correctly detectable in substantially all patients (S. Costagliola et al., J. Clin. Endocrinol. Metab. 84:90-97 (1999).

It is generally known that stimulating autoantibodies (TSAb) which are formed against the TSH receptor and interact with it so that the thyroid gland is stimulated, manifesting as hyperthyroidism, play a role in the thyroid autoimmune disease known as Graves' disease. A characteristic clinical concomitant symptom of Graves' disease which is not attributable directly to the hyperthyroidism is so-called exophthalmos (Graves' ophthalmopathy or GO). The clinical sequels of this concomitant disease range from fairly cosmetic disorders (exophthalmos) to loss of sight. An assumption which is regarded as well founded and is therefore being thoroughly investigated at present is that the autoantibodies typical of the disease and responsible for stimulating the thyroid gland also bind to TSH receptors or variants or fragments thereof which have been detected in retroocular tissue, which, through complex relationships, could lead to an immunogenic inflammation of the ocular muscle tissue and to the typical clinical picture of GO (cf. for example A. P. Weetman, Molecular and Cellular Endocrinology 126 (1997) 113-116).

There are furthermore known cases of hyperthyroidism which are connected to activating mutations of the TSH receptor (cf. Thyroid, Vol. 8, 1998, 559-564, and the relevant literature cited therein), in particular in the case of so-called autonomous thyroid adenoma.

At present three possible treatments based on different principles are available for the treatment of Graves' disease:
a) drug treatment with thiourea derivatives (e.g. carbimazole (INN), methimazole (thiamazole; INN));
b) partial destruction of thyroid tissue by administration of radioactive iodine and
c) surgical removal of the thyroid tissue.

In Germany, many European countries and Japan, drug treatment according to a) is the usual therapy for the first occurrence of Graves' disease. In special situations (for example large goitre, additional suspicions of autonomy), it is also possible immediately to use one of the so-called definitive therapies according to b) or c). In the USA, such therapy according to b) and c) tends to be the rule for historical reasons, and only very few patients (<20%) are treated with drugs according to a).

The drug therapy has advantages and disadvantages. The advantage is that, by the administration of drugs for a limited period, the patient can be brought into a state in which the thyroid function is normalized (euthyroidism) and Graves' disease goes into so-called remission. In the most favourable case, the patient requires no further medication after some time but still has a fully functioning thyroid gland, dispensing with a substitution therapy with thyroid hormones, as required after the definitive therapies according to b) and c).

These so-called definitive therapies lead in most cases to the absence of a fully functioning thyroid gland, and an often life-long substitution therapy with thyroid hormones is necessary to compensate the hypothyroidism caused thereby.

A substantial problem in deciding on the correct therapy is the success to be expected. In principle, success is achieved with all three stated, currently known therapy forms, i.e. remission of the disease can be achieved for a very long time, perhaps even forever. In the case of a successful therapy according to a), no additional therapeutic measures at all would then be necessary. In the case of b) and c), however, the lacking thyroid hormones generally have to be supplied externally in the form of drugs.

However, a common problem of all therapy forms is that so-called recurrence occurs more or less frequently. This means that, after a certain time after the presumed successful therapy, the disease breaks out again, which necessitates further therapeutic interventions. Although such recurrences can occur with all three therapy forms, the drug therapy according to a) is most frequently affected thereby. Thus, only about 50% of all patients suffering from Graves' disease can be brought into remission for a long subsequent period by administration of drugs (tablets) for one to two years.

The drug therapy preferable per se owing to the retention of the thyroid gland has additional disadvantages. On the one hand, the effect of the drugs occurs only after a certain time since they substantially inhibit the synthesis of new hormones but not the release of hormones already formed and stored in the thyroid gland. It thus takes one to two weeks for an effect of the drugs to be evident. In the case of patients with high-grade disease (thyrotoxic crisis), this can result in failure of the treatment. The administration of radioiodine results in a similar situation. Here too, the therapeutic effect occurs only after a delay.

In addition, adverse reactions which require immediate discontinuation of the drugs (agranulocytosis) occur in a few isolated cases under drug treatment. If the patient still remains hyperthyroid, which as a rule is the case, there are only a few therapeutic possibilities. As a result of the adverse reaction of agranulocytosis (complete loss of white blood cells), he is extremely susceptible to infection and is operable only to a limited extent. As a rule, it is therefore impossible to resort to the alternative therapeutic approaches b) and c). In principle, there is therefore a need for further possible therapeutic treatments of Graves' disease, in particular for those which make it possible to retain the thyroid gland and to influence the course of the pathological process.

The use of blocking antibodies against the TSH receptor provides such a further possible therapy which could become established as a fourth therapy form alongside the existing therapeutic treatments and can offer considerable advantages, which will be discussed in more detail further below.

Such a therapy is permitted by the fact that it was possible to prepare selectively blocking antibodies against the TSH receptor in the form of monoclonal antibodies and it was possible to show that these antibodies can actually eliminate the stimulating effect of thyroid-stimulating autoantibodies (TSAb).

The present invention therefore relates, also to those monoclonal blocking antibodies for which a possible preparation and a possible selection are described below in the experimental section and which are additionally made publically available as a precaution by deposition under the designations 4E9/B2/C1 (DSM ACC2389); 4C1/E1/G8 (DSM ACC2390); 1B1/E10/B11/C12 (DSM ACC2391); 7E3/F8/E3 (DSM ACC2392); 3H10/A11/A1 (DSM ACC2393) on 19 Feb. 1999 at DSMZ, Braunschweig, by deposition according to the provisions of the Budapest Treaty.

Blocking antibodies binding to the TSH receptor can be produced and selected in the form of monoclonal antibodies according to the procedure described in the experimental section, in particular after the relatively short amino acid sequence of the extracellular domains of the TSH receptor, to which blocking antibodies of this type or specific, very effective antibodies of this type, bind, have been identified.

As also described in more detail in the experimental section, it was possible to show that, in the bioassay characterized at the outset and using JP09CHO cells, the simultaneous addition of such monoclonal antibodies can selectively suppress the stimulation of these cells by TSH, detectable from the cAMP formation.

The same applies where the stimulation of said cells in the bioassay is effected not by TSH but by addition of sera of patients suffering from Graves' disease and having a high titre of stimulating autoantibodies (TSAb).

The availability of such selective blocking antibodies against the TSH receptor makes it possible to consider a novel therapy of Graves' disease, which is characterized by the use of such blocking antibodies or the use of such antibodies for the preparation of drugs and the administration of such drugs, usually by injection or infusion.

The following may be mentioned as advantages of such a therapy with blocking antibodies:

a) It is to be expected that a rapid inhibition of the stimulation of the TSH receptor is achievable by administering the blocking antibodies, which bind rapidly and with high efficiency to the TSH receptor and block it.
b) The therapy of Graves' disease takes place directly at the place of action of the disease and is thus to be regarded as an aetiological therapy.
c) The therapy with the antibodies can also be used in the case of seriously ill patients for whom the therapy forms known to date fail, without the reservation in such cases about the known therapy form being applicable.
d) Since the target organ of the autoimmune attack can be stabilized by the blocking antibodies, a reduction of the autoimmune process appears to be within the range of possibilities, in analogy to observations of the possibilities of influencing autoimmune processes in other organs.
e) As in the case of the drug treatment, the therapy can be carried out for a limited time with the option of complete remission and retention of the organ.

From the point of view of the principle of action, there are unlikely to be any serious adverse reactions.

The above advantages will be explained in somewhat more detail.

The therapeutic approach using antibodies which block the TSH receptor promises immediate therapeutic success without the delays observed on administration of drugs or radioiodine. The administration of blocking antibodies appears possible even when immediate surgery on a hypothyroid patient is unsuitable. It may therefore be the only option for rapid normalization of the metabolic condition.

In isolated cases where the drug therapy results in agranulocytosis and there are at the time no further possibilities for therapeutic intervention, the use of blocking antibodies may represent a novel alternative treatment which may be life-saving under certain circumstances.

Since the action of stimulating autoantibodies on the TSH receptor is the cause of most clinical symptoms in Graves' disease, the therapeutic administration of blocking antibodies which compete with these pathological stimulating autoantibodies provides the unique opportunity for fighting the course of the pathological process directly at the site of the disease. Such a procedure with therapeutic intervention where a disease has its origin is only very seldom possible.

A further advantage is the expected possibility that the therapy with blocking antibodies has to be carried out only for a limited time, and that the thyroid is retained after the end of the therapy. It is known that, in many cases of Graves' disease, the autoimmune process is of limited duration, i.e. the disease subsides after some time in many cases. The administration of blocking antibodies makes it possible to bridge the acute phase of the disease with clinically relevant symptoms, i.e. is of temporary character similarly to the current drug therapy.

There is moreover reason to hope that the administration of blocking antibodies has an immunomodulatory effect and can lead to a decline in or even curing of the autoimmune process. The blocking of the action of the pathological stimulating antibodies and also the blocking of the physiological TSH put the thyroid gland completely out of action. When the thyroid gland is put out of action in this way, where its metabolism is greatly reduced, the result is reduced expression of antigens or MHCII molecules, which in turn can lead to reduced stimulation of the immune system and to a weakening of the immune response.

Observations made in the case of other autoimmune diseases indicate that such hope is reasonable. Thus, in the case of the autoimmune disease of diabetes mellitus type I, it was shown that the early administration of insulin, making it possible to reduce the endogenous insulin production, is advantageous in a group of patients with a relatively slow course of the disease (cf. Kobayashi et al., Diabetes 45, 622 (1996)). The early insulin administration leads to protection of the insulin-producing cells of the Langerhans' islets, which are less active and are less rapidly destroyed by the autoimmune attack and can thus produce endogenous insulin for a longer time. It may be assumed that putting the thyroid gland out of action by means of blocking antibodies can have similar positive effects.

Furthermore, it is reasonable to hope that the administration of the blocking antibodies can also have a direct positive effect on the immunogenic inflammation which is responsible for the concomitant symptom of Graves' disease, Graves' ophthalmopathy (GO). It has not been possible to date to treat GO aetiologically. In addition to purely symptomatic treatments with, for example, tinted spectacles and eye drops, more aggressive treatments are used in severe cases, in particular in the form of drug therapy with glucocorticoids, high-voltage irradiation of the orbits or surgical decompression of the orbits. However, the successes of the above-mentioned therapies are unsatisfactory. Before such a therapy can be used at all, however, the patient should in any case be euthyroid. Establishing a euthyroid metabolic condition by blocking antibodies according to the present invention therefore also supports the therapy of GO, and the early administration of such antibodies to patients suffering from Graves' disease could also have a prophylactic effect on the development of the ophthalmic symptoms of GO.

The blocking antibodies can also be used for the treatment of specific hyperthyroidisms which are not, as in the case of Graves' disease, based on stimulation of the thyroid gland by autoantibodies but on overstimulation of the thyroid gland by TSH. For example, hyperpituitarism with increased TSH secretion owing to a pituitary adenoma may be mentioned here.

The treatment of hyperthyroidism associated with activating mutations of the TSH by means of the blocking antibodies to be used according to the invention also appears promising. In particular, the observation that the blocking antibodies not only reduce the thyroid function in the presence of stimulating autoantibodies but a reduction in the thyroid function occurs also in normal persons is of importance here (cf. FIG. 2 of the present application, in particular of the value for the controls in the presence of the antibodies 7E3 and 3H10 in comparison with the control without antibodies and the values for the normal sera in FIG. 3).

There are no particular reservations about a therapy with blocking antibodies. There is extensive clinical experience with therapies using antibodies, which in principle are to be regarded as natural substances. It is furthermore known that blocking antibodies, as are to be used in the novel therapy, occur in many patients suffering from Graves' disease without the occurrence of such blocking antibodies being correlated with any effects which are adverse to health.

The blocking antibodies whose preparation and properties are described in the experimental section are not human antibodies but animal (mouse) antibodies, owing to the hybridoma technique used. Said animal antibodies cannot usually be used directly for therapy in human medicine. However, it is now one of the established techniques to "humanize" such animal antibodies for use in human medicine (cf. for example B. R. Glick, J. J. Pasternak, Molekulare Biotechnologie [Molecular Biotechnology], Spektrum Akademischer Verlag Heidelberg, Berlin, Oxford, 1995, page 243 et seq.). The variable Fv fragments of the animal antibodies are coupled with the constant domains and Fc fragments of human antibodies, which results in such humanized (or chimeric) antibodies no longer being recognized as foreign structures and attacked by the human immune system.

The blocking antibodies whose isolation and preparation are described in the experimental section and with which it is demonstrated that they are capable of eliminating the effects of TSH and stimulating antibodies (TSAb) are blocking monoclonal antibodies having specific properties. Owing to their specificity and high affinity for the TSH receptor, they currently appear to be particularly suitable, in humanized form, for use according to the invention for the therapy of Graves' disease. However, this is not intended to exclude from the present invention the use of other antibodies having a blocking action in the same sense against the TSH receptor. Thus, it is not ruled out that there are blocking antibodies which have comparable properties, bind to other amino acid sequences of the TSH receptor, in particular its extracellular domain, and can therefore likewise be used. Furthermore, it is also possible to use polyclonal antibodies which bind with the same effect to one or more sequences of the TSH receptor. The antibodies may furthermore be animal or humanized animal antibodies but may also be human antibodies which were obtained, for example, by selective isolation from suitable patients' sera, or human monoclonal antibodies, as can be prepared, for example, by the technique of so-called EBV transformation (cf. N. G. Morgenthaler et al., J. Clin. Endocrinol. Metab. 81: 3155-3161, 1996). Such antibodies can also be used in the form of their fragments binding specifically to the TSH receptor, for example Fab or Fab' fragments without a Fc part. Furthermore, the antibodies or antibody fragments can also be used in the form of suitable conjugates, bound to carrier molecules, which may be inert but which can also perform additional therapeutic functions. Mixtures of different such antibodies, for example combinations of different monoclonal antibodies, can in principle also be used.

The blocking antibodies to be used according to the invention are those which eliminate the action of TSH and stimulating TSH receptor autoantibodies by binding to the extracellular part of the TSH receptor. They have a sufficiently high affinity to the TSH receptor in order, in concentrations suitable for therapeutic use, successfully to displace or to keep away TSH and stimulating autoantibodies from this TSH receptor.

The autoantibodies to be used according to the invention are administered in a form typical for antibody therapies. Usually, injection solutions, if required infusion solutions, which contain the blocking antibodies intended for the treatment in an aqueous, physiological vehicle medium are provided. The medium may contain the protective or stabilizing additives customary for such media and optionally also nutritional additives or additives promoting the success of the treatment in another way. The presence of further active substances, in particular those influencing the immunological process, is expressly regarded as a possible embodiment of the use, according to the invention, of blocking antibodies for the treatment of Graves' disease.

The amount and concentration of the blocking antibodies to be administered, which is required or recommended for an individual treatment, is optionally to be established while taking into account the individual pathological condition of the patient. Thus, severe symptoms or high titres of TRAb may require the use of larger amounts and higher concentrations of the antibodies to be used according to the invention than less pronounced symptoms with lower autoantibody titres. Suitable amounts and concentrations can be determined empirically from observation of the success of therapy, without particular problems being expected in this respect.

The invention is further explained below by means of experimental results which describe the production, isolation and, with reference to three figures, the testing of monoclonal blocking antibodies against the TSH receptor, as can be made the basis of the uses according to the invention, if required after humanization known per se.

Figure 1:
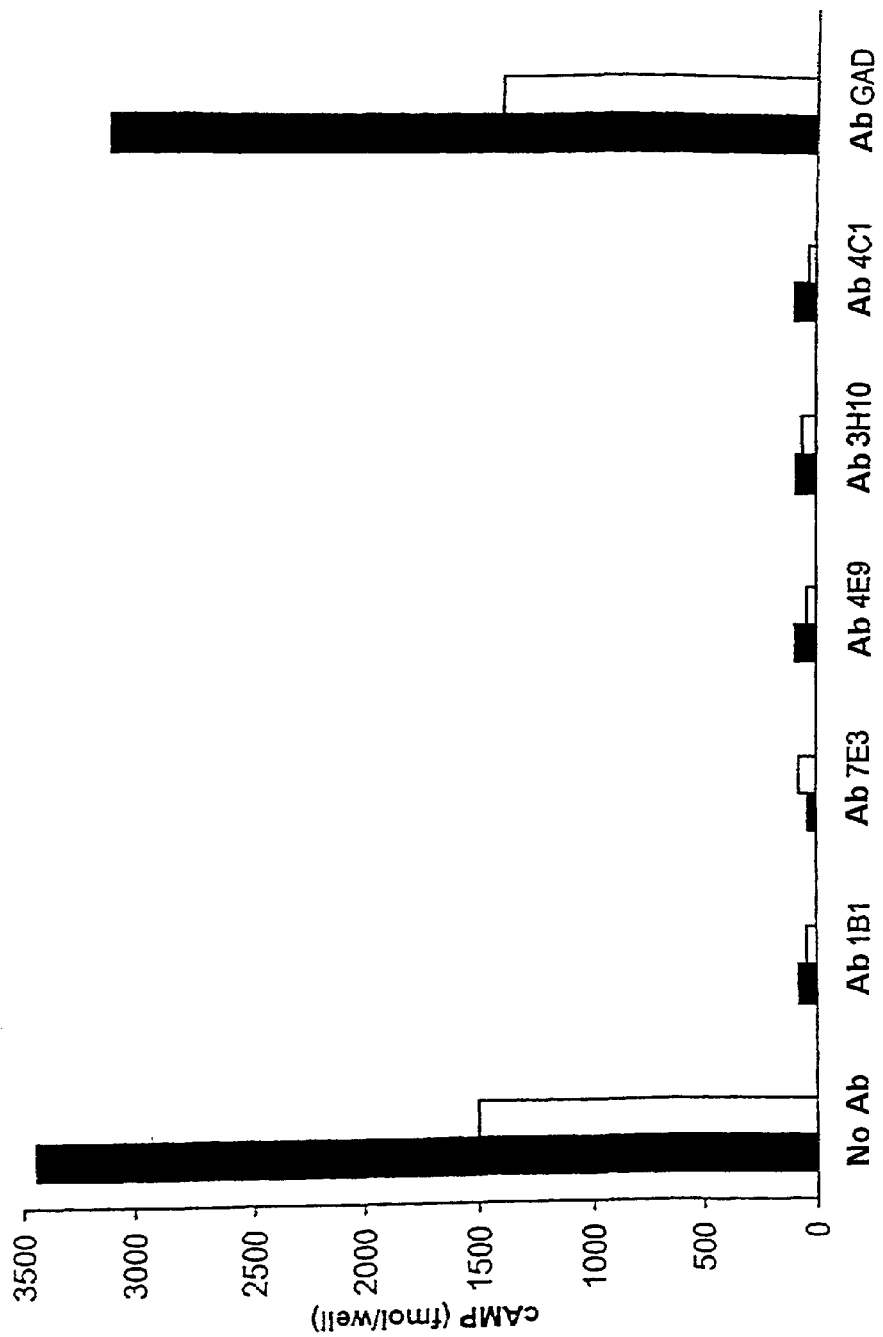
FIG. 1 shows the specific suppression of the cAMP formation of JP09 CHO cells by five monoclonal blocking antibodies in the presence of bovine TSH in the bioassay.

PRODUCTION AND CHARACTERIZATION OF MONOCLONAL BLOCKING ANTIBODIES AGAINST THE HUMAN TSH RECEPTOR

The production, selection and characterization of monoclonal antibodies which can be used according to the invention against the human TSH receptor was carried out substantially with the use of previously described materials and techniques. A detailed description of such materials and techniques has been replaced in the experimental section below by reference to the relevant publications, in so far as comprehension and reworkability are not seriously impaired thereby.

Immunization and Production of Hybridomas

The extracellular domain (ECD) of the human TSH receptor (amino acids 1-415) was prepared in the form of a fusion protein with glutathione-S-transferase in a procaryotic expression system (cf. Harfst, E. et al., J. Mol. Endocrinol. 9, 1992, pages 227-236).

BALB/c mice were immunized with the procaryotically expressed ECD glutathione-S-transferase fusion protein obtained, and the preparation and cloning of hybridomas were carried out as described in more detail in Johnstone, A. P. et al., Mol. Cell. Endocrinol. 105, 1994, R1-R9.

The supernatants of the cloned hybridomas were screened by means of flow cytofluorimetry according to the procedure which is likewise described in Johnstone, A. P. et al., Mol. Cell. Endocrinol. 105, 1994, R1-R9, the previously described cell lines "FLD4" and "FLEA.2" being used as binding reagents. These cell lines are derived from transformed CHO-K1 cells and express different amounts of the functional human TSH receptor of full length, coupled to adenylatecyclase, the multipliable glutamine synthetase expression being used, as described in detail in Harfst, E. et al., Mol. Cell. Endocrinol. 83, 1992, pages 117-123, and Harfst, E., Johnstone A. P., Anal. Biochem. 207, 1992, pages 80-84.

Purification of Monoclonal Antibodies

Hybridomas were grown in spinner cultures in UltraDoma-PF (Bio-Whittaker, Walkerville, Md., USA), containing 2% of FCS and 100 IU/ml of streptomycin. Antibodies were isolated from the supernatants of the tissue cultures by means of affinity chromatography on protein A (using the high salt and pH buffer modifications suitable for IgG1), as described in Johnstone, A. P., Thorpe, R., 1996, Immunochemistry in Practice, 3rd Edition, Blackwell Science Ltd., Oxford.

Characterization of the Antibodies of Various Hybridomas

The antibodies were investigated for their binding behaviour with respect to the recombinant hTSH receptor by immunoprecipitation with cells of recombinant cell lines expressing the hTSH receptor after the in vivo labelling of the receptor protein with [$^{35}$S]-methionine, and furthermore by immunoblotting (or protein blotting) with the extracellular domain of the hTSHR (cf. Harfst E. et al., J. Mol. Endocrinol. 9, 1992, 227-236). In the immunoblotting, the blocked membranes were incubated with extracellular domains of the hTSH receptor for 1-2 h in hybridoma culture supernatant, diluted to a quarter in 200 mM NaCl, 50 mM Tris-HCl, pH 7.4, and then washed. Bound antibodies were detected by means of a second antibody (peroxidase conjugate of an anti-mouse immunoglobulin) and of a commercial chemiluminescence system and were selected on the basis of their reaction with the recombinant hTSH receptor.

The selected monoclonal antibodies were characterized in more detail by means of a cAMP bioassay (Page, S. R. et al., J. Endocrinol. 126, 1990, pages 333-340) and in a radioligand assay with regard to their ability to compete with radiolabelled bovine TSH for the hTSH receptors expressed by the cell lines "FLD4" and "FLEA.2" (see above) (cf. Harfst, E. et al., Mol. Cell. Endocrinol. 83, 1992, pages 117-123, and Harfst, E., Johnstone, A. P., Anal. Biochem. 207, 1992, pages 80-84). For this purpose, hybridoma culture supernatants or the IgG fractions obtained therefrom by purification (purified monoclonal antibodies) and radiolabelled bovine TSH were incubated with said cells, after which the radioactivity bound thereto was determined. The antibodies investigated inhibited the TSH binding.

Determination of the Associated Antibody-Binding Epitopes of the hTSH Receptor

The binding sites (epitopes) of the selected monoclonal antibodies on the extracellular domain of the hTSHR were determined more exactly using a large number of overlapping short synthetic partial peptides from the ECD of the hTSH receptor on cellulose membranes with the aid of a commercial kit (SPOTS kit, Genosys).

It was found that all antibodies selected on the basis of their binding to the hTSH receptor reacted with amino acid sequences from the range of the amino acids 335-390 of the human TSH receptor, and that moreover none of the antibodies in the cAMP bioassay stimulated the cAMP formation of recombinant hTSHR cell lines. Five selected antibodies from stable hybridomas reacted with a short peptide sequence comprising the four amino acids 381-384 of the human TSH receptor (FTSH or Phe Asp Ser His), it being possible to strengthen the binding obtained if the short peptides additionally have up to three of the adjacent amino acids 385 to 387 (YDY or Tyr Asp Tyr) or 378 to 381 (LQA or Le Gln Ala). Those of the selected antibodies which have the highest affinities for the hTSH receptor exhibited 80-90% inhibition of the binding of the radioactive bovine TSH at 1 µg/ml and still more than 50% at 0.1 µg/ml in the above-mentioned competitive radioligand assay.

Agents which can make it considerably easier to identify, in hybridoma supernatants of clones obtained in the reworking of the above-mentioned procedures, those monoclonal antibodies which have suitable binding behaviour in the context of the present invention are now also available in the form of suitably labelled or immobilized peptides which correspond to the above-mentioned sequence 378-387 or a partial sequence thereof.

Inhibition of the Binding of TSAb from Sera of Patients Suffering from Graves' Disease Five monoclonal antibodies which were produced in the experiments described above, which bind to the above-mentioned amino acid sequence 381-384 of the hTSH receptor and which are denoted below by 1B1, 7E3, 4E9, 3H10 and 4C1 were investigated with regard to their suitability for suppressing the binding of bovine TSH and of stimulating autoantibodies from the sera of patients suffering from Graves' disease to a recombinantly expressed hTSH receptor, detectable from stimulation of the cAMP production, in the bioassay mentioned at the outset (N. G. Morgenthaler et al. in Horm. Metab. Res. 30 (1998), pages 162-168).

For this purpose, JP09 CHO cells were incubated in each case with 1 µU (FIG. 1, black bar) or 10 µU (FIG. 1, white bar) of bovine TSH per well and with the addition of the respective antibody to be tested. Another type of antibody (against glutamate decarboxylase; GAD), which showed no activity at all, was also used as a control. The results are shown in FIG. 1, and it is clear that all five antibodies investigated suppress the stimulation of the cAMP production.

Figure 2:
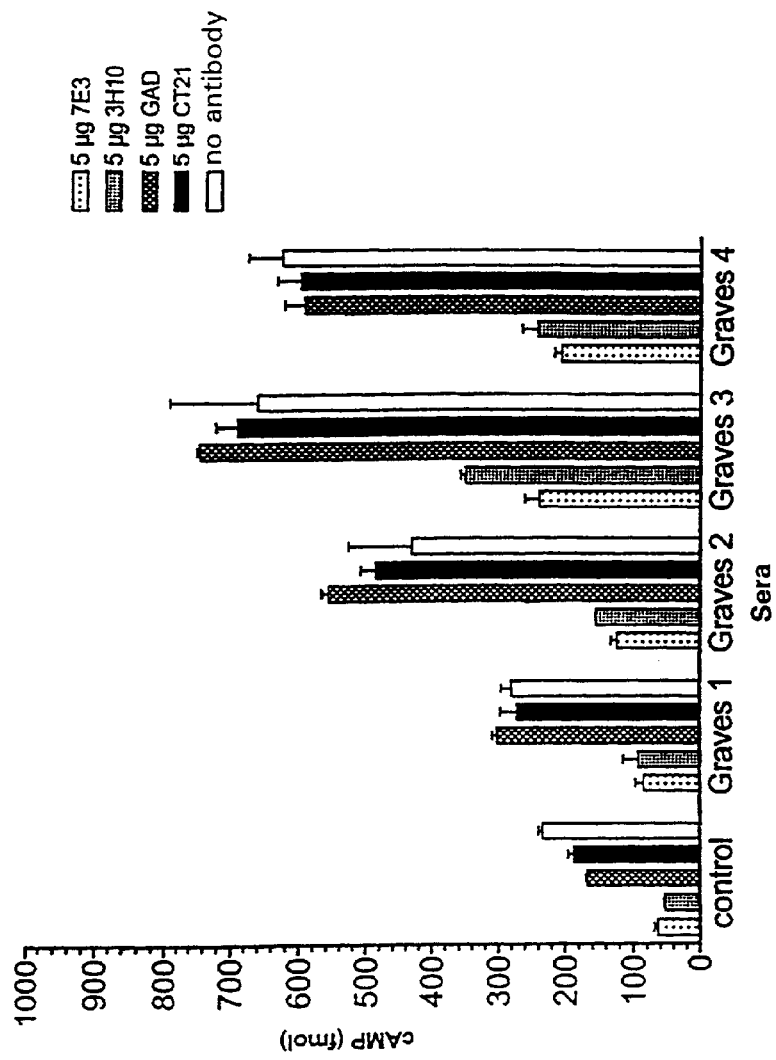
FIG. 2 shows the specific suppression of the cAMP formation of JP09 CHO cells by two monoclonal blocking antibodies in the presence of 4 Graves' disease sera in the bioassay.

The experiment was repeated with the antibodies 7E3 and 3H10 and two antibodies of other types (GAD; CT21), but, instead of the bovine TSH, sera from 4 different patients suffering from Graves' disease were used for stimulating the cAMP production. The results are shown in FIG. 2. It is clear that the formation of cAMP is substantially suppressed in the presence of the antibodies 7E3 and 3H10.

Figure 3:
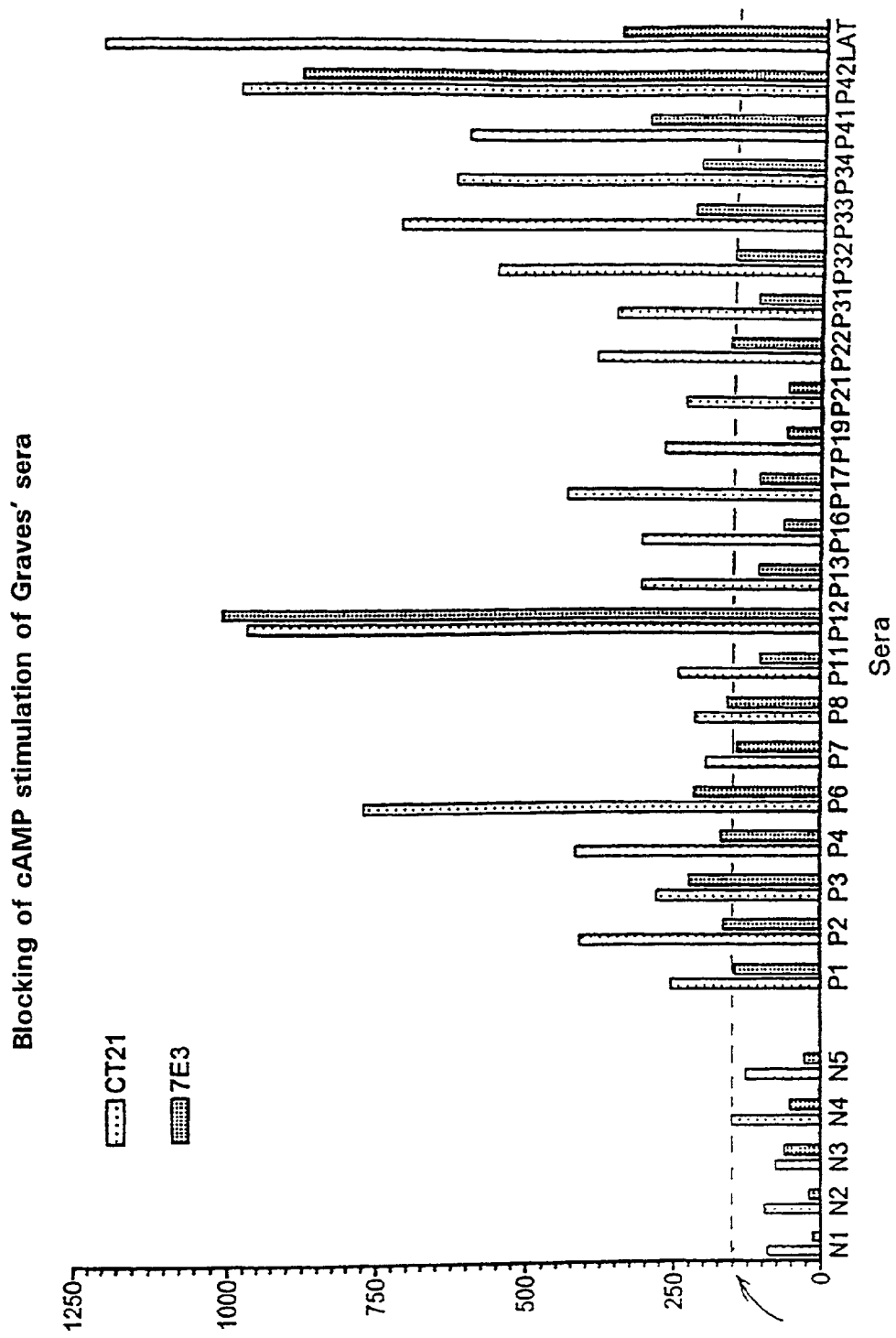
FIG. 3 shows the specific suppression of the cAMP formation of JP09 CHO cells by one monoclonal blocking antibody in the presence of 21 Graves' disease sera and of the LATS standard in the bioassay.

In a further experiment, the suppression of the cAMP production by the antibody 7E3 in the presence of five normal sera (N), 21 sera from patients suffering from Graves' disease (P) and LATS (international standard—long acting thyroid stimulator) was determined in the same bioassay. For comparison, the results were measured again in the presence of another type of antibody (CT21; monoclonal antibody against procalcitonin). The results are shown in FIG. 3. Once again, it is clear that the antibody 7E3 effectively suppresses the formation of cAMP in 20 out of 22 cases.

With regard to the possibility of using blocking antibodies to treat hyperthyroidism on the basis of activating mutations, reference is made to the values for the control sera and normal sera in FIGS. 2 and 3, respectively: in all cases, the cAMP production of the test cells in the presence of the blocking antibodies was noticeably reduced in comparison with antibody-free sera or compared with sera containing antibodies "of another type". This indicates that the blocking antibodies have an effect which goes beyond the pure prevention of the stimulation of the thyroid by TSH or stimulating autoantibodies.

The invention claimed is:

1. An isolated monoclonal antibody against the hTSH receptor wherein said antibody blocks the binding of TSH and/or stimulating autoantibodies with the hTSH receptor, and wherein said antibody specifically binds to an epitope comprising the amino acid sequence FDSH (amino acids 381-384 of the hTSH receptor).

2. An isolated monoclonal antibody wherein said antibody is produced from one of the hybridoma cells deposited under the designations 4E9/B2/C1 (DSM ACC2389); 4C1/E1/G8 (DSM ACC2390); 1b1/E10/B11/C12 (DSM ACC2391); 7E3/F8/E3 (DSM ACC2392); 3H10/A11/A1 (DSM ACC2393) at DSMZ, Braunschweig, according to the Budapest Treaty on 19 Feb. 1999.

* * * * *

SEQUENCE LISTING

```
<160> NUMBER OF SEQ ID NOS: 7

<210> SEQ ID NO 1
<211> LENGTH: 4
<212> TYPE: PRT
<213> ORGANISM: Homo sapiens

<400> SEQUENCE: 1

Phe Asp Ser His
 1
```

```
<210> SEQ ID NO 2
<211> LENGTH: 5
<212> TYPE: PRT
<213> ORGANISM: Homo sapiens

<400> SEQUENCE: 2

Ala Phe Asp Ser His
 1               5

<210> SEQ ID NO 3
<211> LENGTH: 6
<212> TYPE: PRT
<213> ORGANISM: Homo sapiens

<400> SEQUENCE: 3

Gln Ala Phe Asp Ser His
 1               5

<210> SEQ ID NO 4
<211> LENGTH: 7
<212> TYPE: PRT
<213> ORGANISM: Homo sapiens

<400> SEQUENCE: 4

Leu Gln Ala Phe Asp Ser His
 1               5

<210> SEQ ID NO 5
<211> LENGTH: 5
<212> TYPE: PRT
<213> ORGANISM: Homo sapiens

<400> SEQUENCE: 5

Phe Asp Ser His Tyr
 1               5

<210> SEQ ID NO 6
<211> LENGTH: 6
<212> TYPE: PRT
<213> ORGANISM: Homo sapiens

<400> SEQUENCE: 6

Phe Asp Ser His Tyr Asp
 1               5

<210> SEQ ID NO 7
<211> LENGTH: 7
<212> TYPE: PRT
<213> ORGANISM: Homo sapiens

<400> SEQUENCE: 7

Phe Asp Ser His Tyr Asp Tyr
 1               5
```